(12) United States Patent
Moingeon et al.

(10) Patent No.: US 10,610,586 B2
(45) Date of Patent: *Apr. 7, 2020

(54) COMPOSITIONS FOR ANTIGEN-SPECIFIC INDUCTION OF TOLERANCE

(71) Applicant: STALLERGENES, Antony (FR)

(72) Inventors: Philippe Moingeon, Antony (FR); Laurence Van Overtvelt, Antony (FR); Alain Razafindratsita, Antony (FR)

(73) Assignee: STALLERGENES, Antony (FR)

( * ) Notice: Subject to any disclaimer, the term of this patent is extended or adjusted under 35 U.S.C. 154(b) by 396 days.

This patent is subject to a terminal disclaimer.

(21) Appl. No.: 15/240,628

(22) Filed: Aug. 18, 2016

(65) Prior Publication Data

US 2017/0043013 A1 Feb. 16, 2017

Related U.S. Application Data

(63) Continuation of application No. 11/914,815, filed as application No. PCT/IB2006/001310 on May 18, 2006, now Pat. No. 9,555,102.

(30) Foreign Application Priority Data

May 18, 2005 (EP) .................................. 05291073

(51) Int. Cl.

| A61K 39/35 | (2006.01) |
| A61K 9/00 | (2006.01) |
| A61K 47/10 | (2017.01) |
| A61K 47/28 | (2006.01) |
| A61K 47/46 | (2006.01) |
| A61K 39/00 | (2006.01) |

(52) U.S. Cl.
CPC .............. *A61K 39/35* (2013.01); *A61K 9/006* (2013.01); *A61K 47/10* (2013.01); *A61K 47/28* (2013.01); *A61K 47/46* (2013.01); *A61K 2039/542* (2013.01); *A61K 2039/55511* (2013.01); *A61K 2039/55594* (2013.01)

(58) Field of Classification Search
None
See application file for complete search history.

(56) References Cited

U.S. PATENT DOCUMENTS

| 5,192,685 | A | 3/1993 | Yasui |
| 5,244,663 | A | 9/1993 | Bruttmann et al. |
| 6,100,388 | A | 8/2000 | Casas et al. |
| 7,060,687 | B2 | 6/2006 | Hsu et al. |
| 2002/0146429 | A1 | 10/2002 | Ching-Hsaing et al. |
| 2004/0037854 | A1 | 2/2004 | Clancy et al. |
| 2004/0087018 | A1 | 5/2004 | Barrat et al. |
| 2006/0057154 | A1 | 3/2006 | Van Oosterhout et al. |

FOREIGN PATENT DOCUMENTS

| EP | 1184709 A1 | 3/2002 |
| WO | 0137862 A2 | 5/2001 |
| WO | 03063786 A2 | 8/2003 |
| WO | 2005030222 A1 | 4/2005 |

OTHER PUBLICATIONS

Allam et al., "Characterization of dendritic cells from human oral mucosa: A new Langerhans cell type with high constitutive FcɛRI expression" J Allergy Clin Immunol 141-148 (2003).
Allam et al., "Comparative analysis of nasal and oral mucosa dendritic cells" Allergy 61: 166-172 (2006).
Allam et al., Distribution of Langerhans cells and mast cells within the human oral mucosa: new application sites of allergens in sublingual immunotherapy? Allergy 63: 720-727 (2008).
Allam et al., "Toll-like receptor 4 ligation enforces tolerogenic properties of oral mucosal Langerhans cells" J Allergy Clin Immunol 121:368-74 (2008).
Ikeda et al., "Comparison of Mucosal Immune Response after Oral, Nasal or Sublingual Immunization with an Outer Membrane Protein of Porphyromonas Gingivalis" Int J Orai-Med Sci 12{3}:121-128 {2013}.
Kraan et al., "Buccal and sublingual vaccine delivery" Journal of Controlled Release 190:580-592 (2014).
Mascarell et al., "Oral dendritic cells mediate antigen-specific tolerance by stimulating TH1 and regulatory CD41 T cells" J Allergy Clin Immunol122:603-9 (2008).
Moingeon et al., "Immune mechanisms of allergen-specific sublingual immunotherapy" Allergy 61: 151-165 (2006).
Novak et al., "Immunological mechanisms of sublingual allergen-specific immunotherapy Allergy" 66:733-739 (2011).
Ye et al., "Strategies of mucosal immunotherapy for allergic diseases" Cellular & Molecular Immunology 8:453-461 (2011).
Glenting Priority Application—U.S. Appl. No. 60/635,762, filed Dec. 14, 2004.
Glenting Priority Application—Danish Application No. PA200401935, filed Dec. 14, 2004.
Bousquet et al., "Allergen immunotherapy: Therapeutic vaccines for allergic diseases a Who position paper" J. allergy Clin Immunol 10 2(4)(1) Part 1:558-562.
Canonica et al., "Noninjection routes for immunotherapy" J. allergy Clin Immunol, pp. 437-448 (2003).
Murosaki et al., "Heat-killed Lactobacillus plantarum L-137 suppresses naturally fed antigen-specific IgE production by stimulation of IL-12 production in mice" J. allergy Clin Immunol. pp. 57-64 (1998).
Moussu et al., "Bifidobacterium bifidum NCC 453 Promotes Tolerance Induction in Murine Models of Sublingual Immunotherapy" Int Arch Allergy Immunol 158:35-42 (2012).
Mascarell et al., "Oral macrophage-like cells play a key role in tolerance induction following sublingual immunotherapy of asthmatic mice" Mucosal Immunology 4(6):638-647 (2011).

(Continued)

*Primary Examiner* — G. R. Ewoldt
(74) *Attorney, Agent, or Firm* — Browdy and Neimark, PLLC (57) ABSTRACT

The invention relates to an immunogenic composition for sublingual, perlingual or oral administration, comprising at least an antigen and at least an adjuvant that is a bacterium selected from a *Bifidobacterium* and a lactic acid bacterium, and/or a combination of a corticosteroid with vitamin D3 or any metabolite or analog of the latter, in a pharmaceutically acceptable carrier that is suitable for sublingual, perlingual, or oral administration. Such compositions allow to elicit antigen-specific immune tolerance.

16 Claims, 7 Drawing Sheets

(56) References Cited

OTHER PUBLICATIONS

Perdigon et al., "Systemic augmentation of the immune response in mice by feeding fermented milks with *Lactobacillus casei* and *Lactobacillus acidophilus*" Immunology 63:17-23 (1988).

Repa et al. 'Mucosal co-application of lactic acid bacteria and allergen induces counter-regulatory immune responses in a murine model of birch pollen allergy.' Vaccine 22:87-95, 2003.

Van Overveldt et al. 'IL-10-Inducing Adjuvants Enhance Sublingual Immunotherapy Efficacy in a Murine Asthma Model.' Allerg. Immunol. 145:152-162, 2008.

Hols et al. 'Efficient secretion of the model antigen M6-gp41 E in *Lactobacillus plantarum* NCIMB 8826.' Microbial. 143, 2733-2741,1997.

Robinson et al. 'Oral vaccination of mice against tetanus with recombinant *Lactococcus lactis*.' nature. 15:653-657, 1997.

Grangette et al. 'Mucosal immune responses and protection against tetanus toxin after intranasal immunization with recombinant *Lactobacillus plantarum*.' Infect. Immun. 69(3): 154 7-1553, 2001.

Kruisselbrink et al. 'Recombinant *Lactobacillus plantarum* inhibits house dust mite-specific T-cell responses.' Clin. Exp. Immunol. 126:2-8, 2001.

Ishida et al. 'Clinical Effects of *Lactobacillus acidophilus* Strain L-92 on Perennial Allergic Rhinitis: A Double-Blind, Placebo-Controlled Study.' J. Dairy Sci. 88:527-533, 2004.

Norton et al. 'Progress in the development of *Lactococcus lactis* as a recombinant mucosal vaccine delivery system.' 4093):225-230, 1995.

Mercenier et al. 'Lactic acid bacteria as live vaccines.' Curr. Issues Mol. Bioi. 2(1 ):17-25, 2000.

Hawrylowicz et al. 'Potential role of interleukin-10-secreting regulatory T cells in allergy and asthma.' Nat. Rev. Immunol. 5:271-283, 2005.

Adel-Patient et al, "Oral administration of recombinant *Lactococcus lactis* expressing bovine beta-lactoglobulin partially prevents mice from sensitization", Apr. 2005, pp. 539-546, vol. 35, No. 4, Clinical and Experimental Allergy.

Maassen et al, "Instruments for oral disease-intervention strategies: recombinant *Lactobacillus casei* expressing tetanus toxin fragment C for vaccination or myelin proteins for oral tolerance induction in multiple sclerosis" Apr. 23, 1999, pp. 2117-2128, vol. 17, No. 17, Vaccine, Buterworth Scientific Guildford, Great Britain.

Britti et al, "Modulation of the intestinal immuno-response form probiotics", Oct. 2003, pp. 329-337, vol. 32, No. 4, Rivista Di Scienza Dell' Alimentazione.

Adorini et al, "Tolerogenic dendritic cells induced by vitamin D receptor ligands enhance regulatory T cells inhibiting allograft rejection and autoimmune diseases", Feb. 1, 2003, pp. 227-233, vol. 88, No. 2, Journal of Cellular Biochemistry.

Xia et al, "Dexamethasone induces IL-10-producing monocyte-derived dendritic cells with durable immaturity", Mar. 2005, p. A412, vol. 19, No. 2, Suppl. S, Part 1, Experimental Biology 2005 Meeting, San Diego, CA.

Pouwels et al, "The potential of Lactobacillus as a carrier for oral immunization: Development and preliminary characterization of vector systems for targeted delivery of antigens", Jan. 26, 1996, vol. 44, No. 1, Journal of Biotechnology, Amsterdam, NL.

Pouwels et al, "Lactic acid bacteria as antigen delivery vehicles for oral immunization purpose", 1998, pp. 155-167, vol. 41, Microbiology, Amsterdam, NL.

Norton et al, "Protection against tetanus toxin in mice nasally immunized with recombinant *Lactococcus lactis* expressing tetanus toxin fragment C", Apr. 1997, pp. 616-619, vol. 15, No. 6-7, Vaccine, Butterworth Scientific Guildford, Great Britain.

Bermudez-Humaran et al, "Intranasal immunization with recombinant *Lactococcus lactis* secreting murine interleukin-12 enhances antigen-specific Th1 cytokine production" Apr. 2003, pp. 1887-1896, vol. 71, No. 4, Infection and Immunity.

Qiao et al, "Immune responses in rhesus rotavirus-challenged Balb/c mice treated with bifidobacteria and prebiotic supplements", Jun. 2002, pp. 750-755, vol. 51, No. 6, Pediatric Research.

Moreau et al, "Intestinal bacterium and immunomodulation: Adjuvant effect of Biofidobacterium bifidum on the antibody response in an animal model", 1993, pp. 290-292, vol. 29, No. 291, Revue Francaise de Gastro, France.

Xia et al, "Dexamethasone induces IL-10-producing monocyte-derived dendritic cells with durable immaturity", Jul. 2005, vol. 62, No. 1 , Scandinavian Journal of Immunology.

COMPOSITIONS FOR ANTIGEN-SPECIFIC INDUCTION OF TOLERANCE

The present invention relates to adjuvants for sublingual, perlingual or oral immunotherapy.

The sublingual route has been recently explored for antigen administration in a variety of conditions, especially in the field of immunotherapy of allergy. Allergen-specific sublingual immunotherapy (SLIT) indeed represents a safe and efficient non invasive alternative to subcutaneous immunotherapy (see e.g. Bahceciler et al., (2005) *Int. Arch. Allergy Immunol.*, 136:287-294). During SLIT, the allergen is captured within the oral mucosa by Langerhans-like dendritic cells expressing high affinity IgE receptors, producing IL10 (interleukin 10) and TGFβ and upregulating the indoleamine dioxygenase (IDO), suggesting that such cells are prone to induce tolerance.

In this context there is a need for adjuvants that enhance the host immune response to a sublingual administration of antigens and help establish T-cell mediated active tolerance mechanisms.

Immunostimulatory agents or adjuvants have been used for many years to improve the host immune responses to, for example, vaccines.

A wide range of adjuvants can provoke potent immune responses to antigens but are not deprived of toxic effects. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes.

Various safer adjuvants have been proposed. For instance, *Lactobacillus plantarum* was tested for intranasal delivery of heterologous antigens (Grangette et al., (2001) *Infection and Immunity* 69(3) 1547-1553).

All these adjuvants have been used with the aim to trigger T-cell mediated immune effector mechanisms (so called Th1 and/or Th2 responses).

The inventors have now identified adjuvants that elicit antigen-specific regulatory T cells when administered by sublingual, perlingual or oral route.

These T-cell mediated regulatory mechanisms inhibit the above mentioned Th1 and Th2 effector mechanisms, in particular by eliciting an increase in IL10 secretion by T cells.

Such adjuvants are of great interest in immunotherapy of allergic, and other immune disorders.

Although both anergy and T cell depletion are known to contribute to the establishment of peripheral tolerance against self and non-self antigens or environmental allergens, it is now broadly admitted that antigen-specific T cell populations with suppressive/regulatory function play a key role in controlling immune responses to both self and non-self antigens. These cells, termed regulatory T cells, are heterogeneous, and include both: (i) naturally occurring CD4+CD25+ T cells (ii) cells induced in the periphery following antigen exposure (e.g. Tr1 cells, Th3 cells, and CD8+ $T_R$ cells).

The adjuvants identified by the inventors are a bacterium selected from a *Bifidobacterium* and a lactic acid bacterium, and a combination of a corticosteroid and vitamin D3 (or its metabolites, such as 1α,25-dihydroxyvitamin D3, or analogs).

The inventors have notably shown that these adjuvants were liable to induce the secretion of IL10 by T cells in vitro and that they could improve the clinical efficacy of specific immunotherapy in an animal model of asthma.

A subject of the invention is thus an immunogenic composition for inducing antigen-specific tolerance for sublingual, perlingual or oral administration, comprising at least an antigen and at least an adjuvant that is:
  a lactic acid bacterium, and/or
  a combination of a corticosteroid with vitamin D3 or any metabolite or analog of the latter,
in a pharmaceutically acceptable carrier that is suitable for sublingual, perlingual or oral administration. The preferred route of administration is the perlingual route.

The invention further provides a kit comprising:
  in a first container, at least an antigen;
  in a second container, at least an adjuvant that is a *lactobacillus* bacterium, and/or a combination of a corticosteroid with vitamin D3 or any metabolite or analog of the latter;
said antigen and said adjuvant being in pharmaceutically acceptable carriers suitable for sublingual, perlingual or oral co-administration.

These adjuvants are useful for the preparation of an immunogenic composition for sublingual, perlingual or oral administration in association with at least an antigen, for inducing an antigen-specific tolerance, especially for eliciting or improving antigen-specific regulatory T cell responses, in particular by eliciting an increase in IL10 secretion by T cells.

The immunogenic composition that comprises an antigen and such adjuvant is particularly useful for the preparation of a medicament for treating an allergy, an auto-immune disease, or for preventing graft rejection.

The Adjuvant

In one embodiment, the adjuvant is a bacterium selected from a *Bifidobacterium* and a lactic acid bacterium.

Preferably, the bacterium selected from a *Bifidobacterium* and a lactic acid bacterium is a probiotic.

The term "probiotic" relates to bacteria which exert a beneficial effect on a host they are intended to be administered to, by improving the equilibrium of the intestinal flora of said host.

Bifidobacteria include those belonging to the genus Bifidibacterium, such as *Bifidobacterium longum*, *Bifidobacterium bifidum*, *Bifidobacterium infantis* and *Bifidobacterium animalis*.

Lactic acid bacteria include those belonging to the genus *Lactobacillus, Lactococcus* or *Streptococcus*, such as *Lactobacillus plantarum, Lactobacillus delbrueckii, Lactobacillus acidophilus, Lactobacillus fermentum, Lactobacillus casei, Lactobacillus rhamnosus, Lactococcus lactis* and *Streptococcus thermophilus*.

The adjuvant may further be a mixture of at least two bacteria selected from Bifidobacteria and a lactic acid bacteria, in particular at least two lactic acid bacteria, of different genus or species. It may also be one or several mutants thereof, selected for specific immunomodulatory properties.

Preferably the bacteria selected from a *Bifidobacterium* and a lactic acid bacterium, in particular the lactic acid bacterium, is liable to induce IL10 production by T cells.

More preferably, the lactic acid bacterium is a *Lactobacillus*, most preferably *Lactobacillus plantarum*.

The bacteria selected from a *Bifidobacterium* and a lactic acid bacterium, in particular the lactic acid bacterium, may be present in the immunogenic composition of the invention at about 1×10⁸ to 1×10⁹ colony forming units (CFU)/ml, preferably about 5=10⁸ to 1×10⁹ CFU/ml.

In another embodiment, the adjuvant is a combination of a corticosteroid with vitamin D3 or any metabolite or analog of the latter. Preferably the adjuvant is a combination of (i) a corticosteroid and (ii) vitamin D3 or 1α, 25-dihydroxyvitamin D3.

The glucocorticoid used as an adjuvant may be of any type. It may be selected from the group consisting of cortisone, hydrocortisone, beclomethasone, flunisolide, prednisone, prednisolone, methylprednisolone, triamcinolone, deflazacort, betamethasone, dexamethasone, diflorasone, fluticasone, halobetasol, budesonide, clobetasol, fluocinolone, and triamcinolone, or any pharmaceutically acceptable salt thereof. Preferably it is dexamethasone or fluticasone. Most preferably it is dexamethasone.

As used herein the term "vitamin D3" means cholecalciferol. Its metabolites or analogs include 1 α,25-dihydroxyvitamin D3 and any of cholecalciferol;

1 α,25-dihydroxy-26,27-hexafluorocholecalciferol;

1α,25-dihydroxy-22-ene-26,27-hexafluorocholecalciferol;

1α,25-dihydroxy-26,27-hexafluoro-16-ene-23-yne-cholecalciferol;

1α,25-dihydroxy-23-yne-cholecalciferol;

1 α,25-dihydroxy-16-ene-cholecalciferol;

1α,25-dihydroxy-16-ene-23-yne-cholecalciferol;

26,26,26,27,27,27-hexafluoro-1α-fluoro-25-hydroxy-16-ene-23-yne-cholecalciferol;

26,26,26,27,27,27-hexafluoro-1α-25-dihydroxy-16-ene-23-yne-19-nor-cholecalciferol;

26,26,26,27,27,27-hexafluoro-25-hydroxy-16-ene-23-yne-19-nor-cholecalciferol; and 26,26,26,27,27,27-hexafluoro-1α-fluoro-25-hydroxy-16-ene-23-yne-19-nor-cholecalciferol.

A preferred combination is dexamethasone and 1 α,25-dihydroxyvitamin D3.

In a particular embodiment, the combination of vitamin D3 or its metabolites or analogs, and corticosteroid, may be present in the following proportions:

vitamin D3 (or its metabolites or analogs)/corticosteroid: 0.001 to 0.01%, preferably about 0.003% (w/w);

adjuvant (vitamin D3 or its metabolites or analogs+ corticosteroid)/antigen: 1 to 10%, preferably about 4% (w/w);

adjuvant (vitamin D3 or its metabolites or analogs+ corticosteroid)/whole composition: 1 to 10%, preferably about 3 to 5%, preferably about 4% (w/w).

The Antigen

The antigen may be of any type. It can be a protein, a polypeptide or a peptide, a carbohydrate, a lipid, or a nucleic acid.

Peptides having defined amino acid sequences and which comprise T cell epitopes, may be identified for any protein antigen or autoantigen. One method includes dividing the protein antigen into non-overlapping, or overlapping peptides of desired lengths and synthesizing, purifying and testing those peptides to determine whether the peptides comprise at least one T cell epitope using any number of assays (e.g. T cell proliferation assays, lymphokine secretion assays, and T cell non-responsiveness studies). In another method an algorithm is used for predicting those peptides which are likely to comprise T cell epitopes and then synthesizing, purifying and testing the peptides predicted by the algorithm in T cell assays to determine if such predicted peptides cause T cell proliferation or lymphokine secretion, or T cell non-responsiveness and are therefore likely to contain T cell epitopes.

In a preferred embodiment, the antigen is an allergen. An "allergen" is defined as a substance, usually a protein, which elicits the production of IgE antibodies in predisposed individuals Similar definitions are presented in the following references: *Clin. Exp. Allergy*, No. 26, pp. 494-516 (1996); *Mol. Biol. of Allergy and Immunology*, ed. R. Bush, Immunology and Allergy Clinics of North American Series (August 1996).

Preferably the antigen is a protein allergen, which means any amino acid chain likely to trigger an allergic response, including short peptides of about 6 to 20 amino acids, polypeptides, or full proteins.

Preferably the protein allergen is selected from the group consisting of a protein allergen of the genus *Dermatophagoides*; a protein allergen of the genus *Felis*; a protein allergen of the genus *Ambrosia*; a protein allergen of the genus *Lolium*; a protein allergen of the genus *Cryptomeria*; a protein allergen of the genus *Alternaria*; a protein allergen of the genus *Alder*; a protein allergen of the genus *Betula*; a protein allergen of the genus of *Blomia*; a protein allergen of the genus *Quercus*; a protein allergen of the genus *Olea*; a protein allergen of the genus *Artemisia*; a protein allergen of the genus *Plantago*; a protein allergen of the genus *Parietaria*; a protein allergen of the genus *Canine*; a protein allergen of the genus *Blattella*; a protein allergen of the genus *Apis*; a protein allergen of the genus *Cupressus*; a protein allergen of the genus *Thuya*; a protein allergen of the genus *Chamaecyparis*; a protein allergen of the genus *Periplaneta*; a protein allergen of the genus *Agropyron*; a protein allergen of the genus *Secale*; a protein allergen of the genus *Triticum*; a protein allergen of the genus *Cynorhodon*; a protein allergen of the genus *Juniperus*; a protein allergen of the genus *Dactylis*; a protein allergen of the genus *Festuca*; a protein allergen of the genus *Poa*; a protein allergen of the genus *Avena*; a protein allergen of the genus *Holcus*; a protein allergen of the genus *Anthoxanthum*; a protein allergen of the genus *Arrhenatherum*; a protein allergen of the genus *Agrostis*; a protein allergen of the genus *Phleum*; a protein allergen of the genus *Phalaris*; a protein allergen of the genus *Paspalum*; and a protein allergen of the genus *Sorghum*.

Examples of various known protein allergens derived from some of the above-identified genus include: *Betula* (*verrucosa*) Bet v I; Bet v II; *Blomia* Blo t I; Blo t III; Blo t V; Blo t XII; *Cynorhodon* Cyn d I; *Dermatophagoides* (*pteronyssinus* or *farinae*) Der p I; Der p II; Der p III; Der p VII; Der f I; Der f II; Der f III; Der f VII; *Felis* (*domesticus*) Fel d I; *Ambrosia* (*artemiisfolia*) Amb a I.1; Amb a I.2; Amb a I.3; Amb a I.4; Amb a II; *Lollium* (*perenne*) Lol p I; Lot p II; Lol p III; Lot p IV; Lol p IX (Lol p V or Lol p Ib); *Cryptomeria* (*japonica*) Cry j I; Cry j II; Can f I; Can f II; *Juniperus* (*sabinoides* or *virginiana*) Jun s I; Jun v I; *Juniperus* (*ashei*) Jun a I; Jun a II; *Dactylis* (*glomerata*) Dac g I; Dac g V; *Poa* (pretensis) Poa p I; Phl p I; Phl p V; Phl p VI and *Sorghum* (*halepensis*) Sor h I.

In addition, similar to allergy, autoimmune diseases such as type I diabetes, multiple sclerosis, and rheumatoid arthritis are generally accepted as being the result of an antigen specific T cell mediated response against an antigen which in the case of autoimmune disease is an autoantigen, i.e. an antigen that belongs to the body's own tissue. The same applies to the phenomenon of graft rejection, where the antigen belongs to the graft tissue, possibly coming from another individual or even from another animal species.

In another embodiment, the antigen is involved in an autoimmune disease or graft rejection.

A number of antigens (i.e. autoantigens) have been found to cause symptoms in autoimmune diseases (i.e. autoantigens such as insulin; myelin basic protein; rh factor; acetylcholine receptors; thyroid cell receptors; basement membrane proteins; thyroid proteins; ICA-69 (PM-1); glutamic acid decarboxylase (64K or 65 K); proteolipid protein (PLP), myelin associated glycoprotein (MAG), collagen (type II), heat shock protein and carboxypeptidase H) such as diabetes, rheumatoid arthritis, and multiple sclerosis.

Immunogenic Compositions and Kits

The antigen and the adjuvant as above defined are either combined in an immunogenic composition or are presented separately, for a co-administration.

One may employ one or several antigens. The immunogenic composition comprises at least an adjuvant as defined above, that is to say that one may also employ additional adjuvants.

The antigen and the adjuvant are associated with a pharmaceutically acceptable carrier that is suitable for sublingual, perlingual (i.e. through the tongue mucosa) or oral administration. The antigen and the adjuvant can also be co-administered in the form of separate compositions. The co-administration means either simultaneous or consecutive administration of said compositions.

As used herein, the term "pharmaceutically acceptable carrier" includes solvents, dispersion media, coatings, isotonic and absorption delaying agents, mucoadhesive excipients, and the like, that do not produce an adverse or other untoward reaction when administered to an animal, or a human, as appropriate.

Preferred sublingual, perlingual or oral dosage forms include solid forms, adhesive tablets, biofilms or creams, ointments, powders, gels, and pastes. A preferred form is a tablet, e.g. as those described in U.S. Pat. No. 5,244,663. The sublingual or perlingual dosage unit is manufactured to disintegrate rapidly. The time period for complete disintegration of the dosage unit is typically in the range of from about 10 seconds to about 30 minutes, and optimally is less than 5 minutes.

Carriers may further include, but are not limited to disintegrants, binders, lubricants, flavoring, colorants, preservatives. Suitable disintegrants include dry starch, calcium carbonate, polyoxyethylene sorbitan fatty acid esters, sodium lauryl sulfate, stearic monoglyceride, lactose, as well as cross-linked polyvinylpyrrolidones, such as crospovidone (e.g., Polyplasdone™. XL, which may be obtained from GAF), cross-linked carboxylic methylcelluloses, such as croscarmelose (e.g., Ac-di-Sol™ which may be obtained from FMC), alginic acid, and sodium carboxymethyl starches (e.g., Explotab™, which may be obtained from Edward Medell Co., Inc.), methylcellulose, agar bentonite and alginic acid. Binders, if used, are those that enhance adhesion. Examples of such binders include, but are not limited to, starch, gelatin and sugars such as sucrose, dextrose, molasses, and lactose. Preferred lubricants are stearates and stearic acid.

Lactose, mannitol, and croscarmelose are preferred excipients.

Additional components that may be incorporated into the dosage forms are known, or will be apparent, to those skilled in this art; for example, see Remington: The Science and Practice of Pharmacy, 19th edition (Mack Publishing, 1995).

In another embodiment the immunogenic composition is in a liquid form.

The composition can be administered as dry powder particles or as an atomized aqueous solution suspended in a carrier gas (e.g. air or $N_2$). Preferred aerosol formulations may comprise for example, a physiologically-acceptable buffered saline solution containing between about 1 μg and about 300 μg of the antigens.

For the preparation of aqueous suspensions and/or elixirs, one may employ various sweetening or flavouring agents, colouring matter and, if so desired, emulsifying and/or suspending agents, together with such diluents as water, ethanol, propylene glycol, glycerine and various combinations thereof. Glycerine is preferred.

The immunogenic composition is preferably administered to the patient under the tongue. The sublingual mucosa, located on the underside of the tongue, facilitates capture of the antigen and adjuvant by Langerhans-like cells that migrate to draining lymph nodes to prime T lymphocytes.

For example, recombinant Bet v I protein allergen has been formulated as a tablet for sublingual administration.

When it is in liquid form, the composition can be administered under the tongue by placing one or more drops underneath the tongue or by spraying the underside of the tongue with a preselected volume of the liquid composition. Preferably, the administered volume, either drops or spray, is less than about 1 ml.

A route of administration of particular interest is to keep the composition under the tongue a few minutes, e.g. about 2 minutes, before swallowing it.

The present invention further provides a kit comprising:
in a first container, at least an antigen;
in a second container, at least an adjuvant that is a lactic acid bacterium, said antigen and said adjuvant being in pharmaceutically acceptable carriers suitable for sublingual, perlingual or oral co-administration.

Another subject of the invention is a kit comprising:
in a first container, at least an antigen;
in a second container a corticosteroid;
in a third container, vitamin D3 or any metabolite or analog of the latter;
each being in pharmaceutically acceptable carriers suitable for sublingual, perlingual or oral co-administration.

A further subject of the invention is a kit comprising:
in a first container, at least an antigen;
in a second container a combination of a corticosteroid and vitamin D3 or any metabolite or analog of the latter;
each being in pharmaceutically acceptable carriers suitable for sublingual, perlingual or oral co-administration.

When the antigen and the adjuvant are co-administered in separate compositions or provided as a kit, they can be in different types of carriers, both suitable for sublingual, perlingual or co-administration. For instance, the antigen may be in the form of a solid composition, while the adjuvant is in a liquid composition.

Immunotherapy

The association of an antigen with the adjuvant as defined above elicits or improves antigen-specific regulatory T cell responses.

The immunogenic compositions that combine an antigen with the adjuvant can be used as a vaccine, or in a therapeutic or prophylactic treatment regimen for the prevention of, or delay in, the onset of disease symptoms caused by an offending antigen or results in reduction, progression, or alleviation of symptoms caused by an offending antigen, i.e. down regulation of an antigen specific immune response. The kits disclosed herein are similarly useful.

Immunotherapy of allergies generally comprises desensitization or hyposensitisation, which is a treatment consisting in administering to the patient progressively increasing doses of the allergen(s) to which the patient has developed or is likely to develop a sensitivity.

There is further provided a method for preventing or treating an allergy, which method comprises administering to a subject in need thereof an antigen and the adjuvant as described above, e.g., in the form of an immunogenic composition, wherein the antigen is an allergen.

There is further provided a method for treating an autoimmune disease, which method comprises administering to a subject in need thereof an antigen and the adjuvant as described above, e.g., in the form of an immunogenic composition, wherein the antigen is involved in the autoimmune disease. Non-limiting examples include rheumatoid arthritis, multiple sclerosis, endocrine ophthalmopathy, uveoretinitis, Type 1 diabetes, systemic lupus erythematosus; sclerodermia, myasthenia gravis, Grave's disease, glomerulonephritis, autoimmune hepatological disorder, autoimmune inflammatory bowel disease, and Crohn's disease.

The antigen and the adjuvant as described above, e.g. in the form of an immunogenic composition, are also useful in the treatment of recipients of tissue or organ transplants to reduce host-induced allograft rejection.

There is further provided a method for preventing a graft rejection, which method comprises administering to a subject in need thereof an antigen and the adjuvant as described above, e.g., in the form of an immunogenic composition, wherein the antigen belongs to the graft tissue and is likely to cause graft rejection.

The subject is preferably a human, regardless of the age, sex, and condition. It may also be any other mammal, including pets such as cats or dogs.

The example and figures below illustrate the invention without limiting its scope.

LEGENDS TO THE FIGURES

FIG. 1: Experimental Design

A. Sensitization was performed by two intraperitoneal (i.p.) injections in 14 days interval with 10 µg ovalbumin (OVA) or phosphate buffer saline (PBS) (control) adsorbed to 2 mg Al(OH)$_3$. The sensitization was followed by a 20 min aerosol challenge with 1% w/v OVA on 5 consecutive days. Blood samples (bleeding) were taken after sensitization in order to perform the anti-OVA antibody titration. Measurements of airway responsiveness were performed by whole body plethysmography. After sacrifice of mice, spleen cells and lung were isolated for cytokine analysis and inflammation detection respectively.

For tolerance induction in a therapeutic model, sensitized mice were sublingually treated with PBS (control), OVA or OVA plus adjuvant every week, twice a week, during 2 months at a concentration of 500 µg. Blood samples (bleeding) were taken for humoral response analysis. Measurements of airway responsiveness were performed by whole body plethysmography. After sacrifice of mice, spleen and lung were removed for in vitro cytokine assays and inflammation analysis respectively.

B. For tolerance induction in a prophylactic model, mice were sublingually treated with PBS, OVA or OVA plus adjuvant every week, twice a week, during 1 month at a concentration of 500 µg. Sensitization was performed by two intraperitoneal (i.p.) injections in 14 days interval with 10 µg ovalbumin (OVA) or phosphate buffer saline (PBS) (control) adsorbed to 2 mg Al(OH)$_3$. The sensitization was followed by a 20 min aerosol challenge with 1% w/v OVA on 5 consecutive days. Blood samples (bleeding) were taken for humoral response analysis. Measurements of airway responsiveness were performed by whole body plethysmography. After sacrifice of mice, spleen and lung were removed for in vitro cytokine assays and inflammation analysis respectively.

FIG. 2: Humoral, Cellular, Respiratory Responses, and Inflammation after Sensitization A. OVA-specific IgG1 and IgG2a (dilution 1/100) antibody levels were measured in sera from 4 mice sensitized with OVA.

B. OVA-specific IgE (dilution 1/10) antibody level was measured in sera from 3 mice sensitized with OVA.

C. IFN-γ, IL-5 and IL10 levels in spleen cell of mice sensitized with OVA were measured by Elispot.

D. The airway responsiveness was determined for sensitized mice with PBS or OVA by measurement of Penh index in response to methacholine (50 mg/ml). Eight mice per group were displayed (▲=mean).

E. Representative lung sections obtained 48 h after the last challenge. Paraffin tissue sections were stained with HES (Hematoxylin, eosin, safran). One arrow (top) indicates bronchial mucus secretion and the other arrow (bottom) indicates specific cellular infiltration.

FIG. 3: Airway Responsiveness after Tolerization

The airway responsiveness was determined for healthy mice, mice sensitized with OVA and tolerized with PBS, mice sensitized with OVA and tolerized with OVA) and mice sensitized with OVA and tolerized with OVA+dexamethasone (Dex)+1α,25-dihydroxyvitamin D3 (vitD3) (panel A) or OVA+*L. plantarum* (panel B)) by measurement of Penh value in response to methacholine (50 mg/ml). Four to eight mice per group were displayed (horizontal bar=median).

FIG. 4: TGF-β Production after Tolerization

TGF-β production was determined for group 1 (sensitized OVA and tolerized PBS, n=2), group 2 (sensitized OVA and tolerized OVA, n=3) and group 3 (sensitized OVA and tolerized OVA+VitD3+Dex n=4 (panel A) or OVA+*L. plantarum* n=3 (panel B)) by Elipsot.

EXAMPLE

Sublingual Administration of Ovalbumin with (i) *Lactobacillus plantarum* or (ii) 1α,25-Dihydroxyvitamin D3+Dexamethasone:

SUMMARY

Adjuvants inducing IL10 gene expression by human T cells in vitro (*Lactobacillus plantarum* or 1α,25-dihydroxyvitamin D3+dexamethasone) were mixed with ovalbumin and administered sublingually to Balb/c mice sensitized to ovalbumin. When compared with ovalbumin alone or untreated animals, each of those adjuvants could enhance the clinical efficacy of the vaccine (based on improvement of the respiratory function). Clinical improvement was correlated with an increase in ovalbumin-specific TGFß producing T lymphocytes in the spleen (i.e. T cells with a regulatory profile, subtype Tr1 or Th3).

Materials and Methods:
1. Animals, Culture Medium, Reagents and Antigens

Six-week-old female BALB/c mice were purchased from Charles River (L'Arbresle, France) and maintained on an ovalbumin-free diet. Each experimental group consisted of two to eight mice. The international levels of ethical standards for the use of animals were applied.

Culture medium for spleen cell consisted of RPMI 1640 containing 10% fetal calf serum and 1% L-glutamine (all from Invitrogen, France).

Ovalbumin (OVA, Garde V) was purchased from Sigma Chemicals. Phosphate-buffer saline (PBS) and alum were purchased from Invitrogen (France) and Pierce (Rockford, Ill.), respectively.

2. Adjuvants

A strain of lactic acid bacteria (LAB), *Lactobacillus plantarum*, was used for in vivo applications in BALB/c mice (Microbiologies, Inc., Saint Cloud) at $2 \times 10^8$ colony forming units (CFU)/ml in sterile PBS.

1a,25-dihydroxyvitamin D3 (1 mg/kg) and dexamethasone (0.03 μg/kg) in sterile PBS were also used.

Figure 1A:
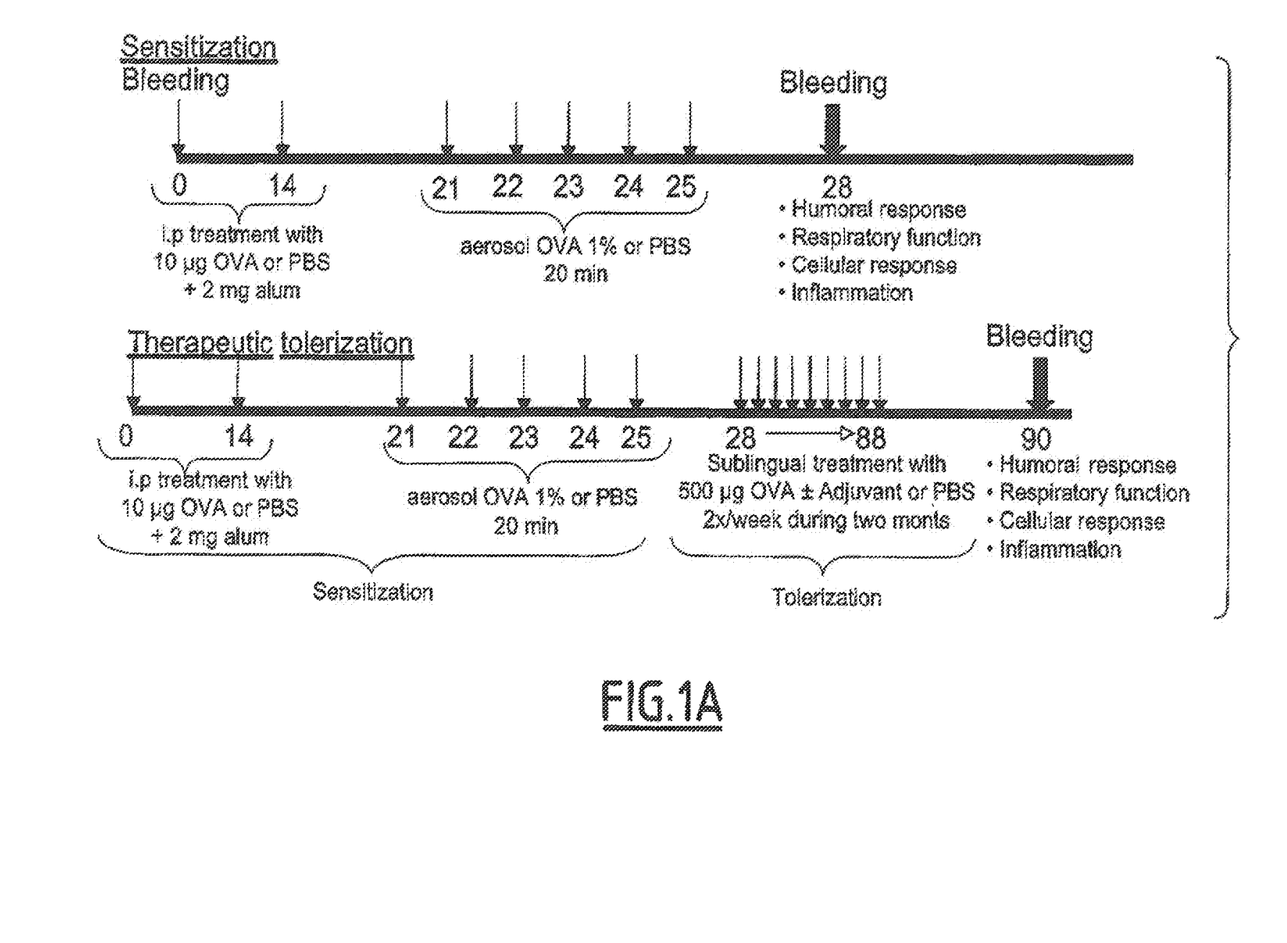
Figure 1B:
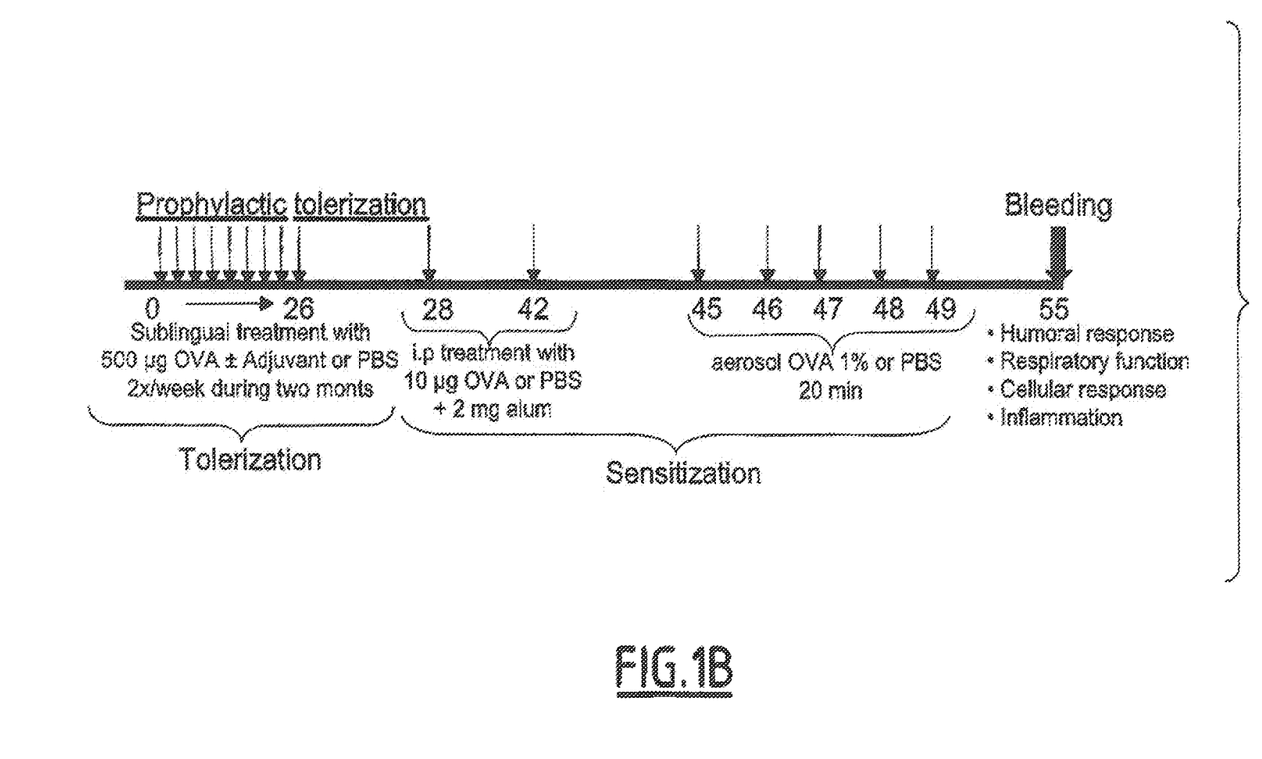

3. Mice Sensitization and Tolerization (FIG. 1)

Sensitization was performed by two intraperitoneal (i.p.) injections in 14 days interval with 10 μg OVA adsorbed to 2 mg Al(OH)$_3$ in a total volume of 100 μl. The sensitization was followed by a 20 min aerosol challenge with 1% w/v OVA on 5 consecutive days with an aerosol delivery system (Buxco Europe; Ltd, UK). Control animals were sham treated with sterile PBS.

For tolerance induction in a therapeutic model, sensitized mice were sublingually treated with OVA or OVA plus adjuvant every week, twice a week, during 2 months at a concentration of 500 μg (20 μl). Control mice were sensitized with OVA followed by sham tolerization with PBS.

For tolerance induction in a prophylactic model, mice were sublingually treated with PBS, OVA or OVA plus adjuvant every week, twice a week, during 1 month at a concentration of 500 μg. Sensitization was performed by two intraperitoneal (i.p.) injections in 14 days interval with 10 μg ovalbumin (OVA) or phosphate buffer saline (PBS) (control) adsorbed to 2 mg Al(OH)$_3$. The sensitization was followed by a 20 min aerosol challenge with 1% w/v OVA on 5 consecutive days.

4. Determination of Airway Responsiveness

Measurements of airway responsiveness were performed by whole body plethysmography (Buxco Europe; Ltd, UK), 48 h after the last challenge for sensitisation or tolerization. Airflow signals were recorded in response to aerosolized methacholine (50 mg/ml), 1 minute, four times. The higher value of Penh (enhanced pause) was taken into account for the calculation of the Penh index (Penh index=Penh measured/Penh PBS).

5. Determination of Serum Allergen-Specific Antibody Levels

Blood samples were collected after the sensitization in order to perform the anti-OVA antibody titration by ELISA. For detection of IgG1 and IgG2a antibodies, the mouse anti-serum was incubated with purified OVA (0.1 μg) coated onto ELISA plates (Nunc, Denmark). Biotinylated-rat anti-mouse IgG1 or IgG2a antibodies (dilution 1/100, BD Pharmingen) were applied and streptavidin-peroxidase-conjugated rat anti-mouse IgG antibodies (dilution 1/400, BD Pharmigen) were used for detection. An o-phenylene diamine and hydrogen peroxide substrate (Sigma) was added, the reaction stopped and the optic density (OD) read using an ELISA reader at 492 nm.

For detection of IgE antibody; mouse IgE antibodies (Bethyl Laboratories) were coated onto ELISA plates. The mouse anti-serum was applied and OVA-digoxigenin (dilution 1/20, Roche) plus HRPO-conjugated rabbit anti-digoxigenin (dilution 1/1000, Roche) were used for detection. An ABTS substrate was added (Roche), the reaction stopped and the OD read using an ELISA reader at 405 nm.

6. Dosage of TGF-β

Dosage of TGF-β from supernatants of spleen cell cultures was performed with an ELISA kit (R&D systems).

7. Spleen Cell Cultures for Cytokine Analysis by Elispot

Mice were killed by cervical dislocation. Spleens cells were isolated and plated in triplicate in 96-well flat-bottomed ELISPOT plates (Millipore, Massachussets) at densities of $2 \times 10^5$ cells per well. Different conditions were used: medium alone, OVA (100μg/ml) and PMA (phorbol myristyl acetate) (50 ng/ml, Sigma)/ionomycin (500 ng/ml, Sigma) which was used as positive control. Spot forming cells (SFCs) were monitored for IFN-γ, IL-5 and IL10. Elispot kits were from R&D systems Europe.

8. Lung Histology

Mice were killed by cervical dislocation. Lungs were isolated and embedded in paraffin. Micrometer paraffin sections were stained with HES (hematoxylin, eosin, safran).

9. Gene Expression by Human T Cells

Dendritic cells DC were treated with candidate adjuvants for 24 h, washed and cultured with purified allogenic naïve CD4+ T cells. mRNAs were extracted 24 h to 5 days later and gene expression was assessed by quantitative PCR with primers specific for the tested genes. Only data above 2-fold increase were considered as significant.

Results

A. Selection of IL-10-Inducing Adjuvants in Human In Vitro Model

A human in vitro model, consisting of a coculture of human pretreated DC with allogenic T cells, has been used to select IL-10-inducing adjuvants. Briefly, human DC were treated with adjuvants. After 24 h, the DC were washed and cultured with allogenic naive CD4+ T cells. After 24 h to 5 days, gene expression in human T cells was assessed by quantitative PCR.

Among several putative adjuvants tested, *Lactobacillus plantarum* and 1α,25-dihydroxyvitamin D3 in combination with dexamethasone (Vit/Dex) have been shown liable to induce IL10 gene expression by human T cells in vitro (Table 1).

TABLE 1

Summary of screening data for IL10 inducing adjuvants

| | Gene expression by T cells | | | | | |
|---|---|---|---|---|---|---|
| Adjuvants | Tbet | IFN | GATA3 | Foxp3 | TGF | IL10 |
| Vit/Dex | − | − | + | + | + | +++ |
| *L. plantarum* | − | +++ | − | − | − | ++ |
| R848 | − | + | − | − | − | − |
| LTA | − | ++ | − | − | − | − |
| Pam3CSK4 | − | − | − | − | − | − |
| LPS pg | − | − | − | − | − | − |
| Imiquimod | − | − | + | − | + | − |
| ssPolyU | − | − | − | − | − | − |

B. Immunotherapy Experiments

1. Murine Models of Sensitization with OVA

Figure 2A:
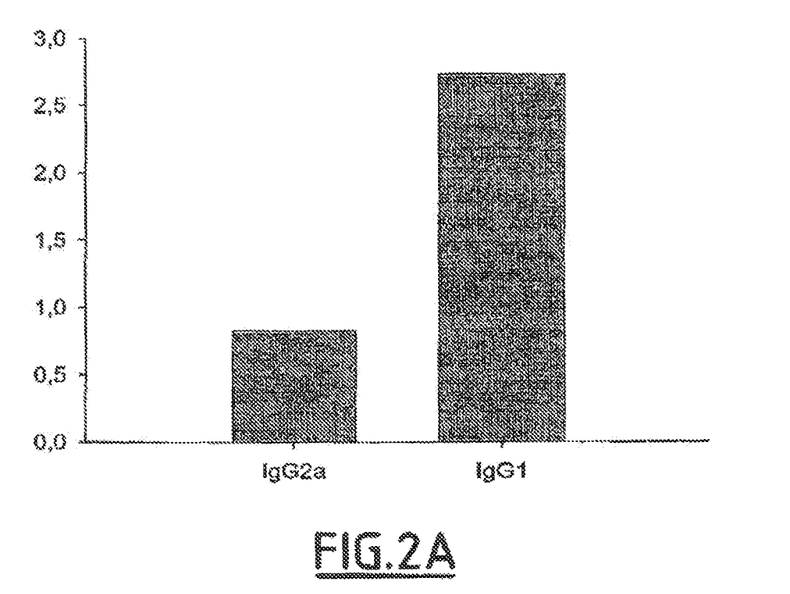
Figure 2B:
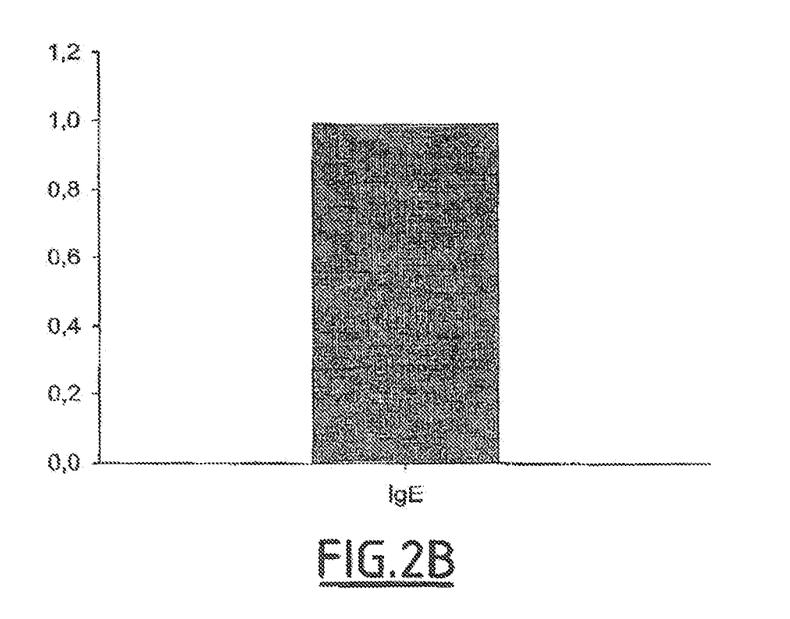
Figure 2C:
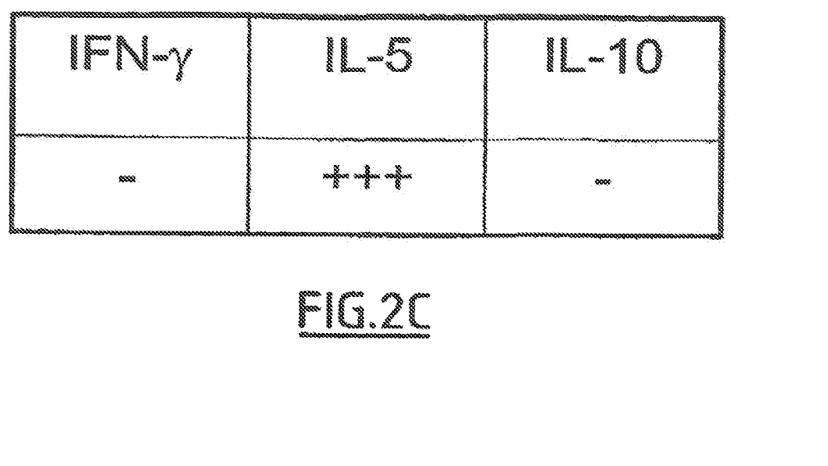
Figure 2D:
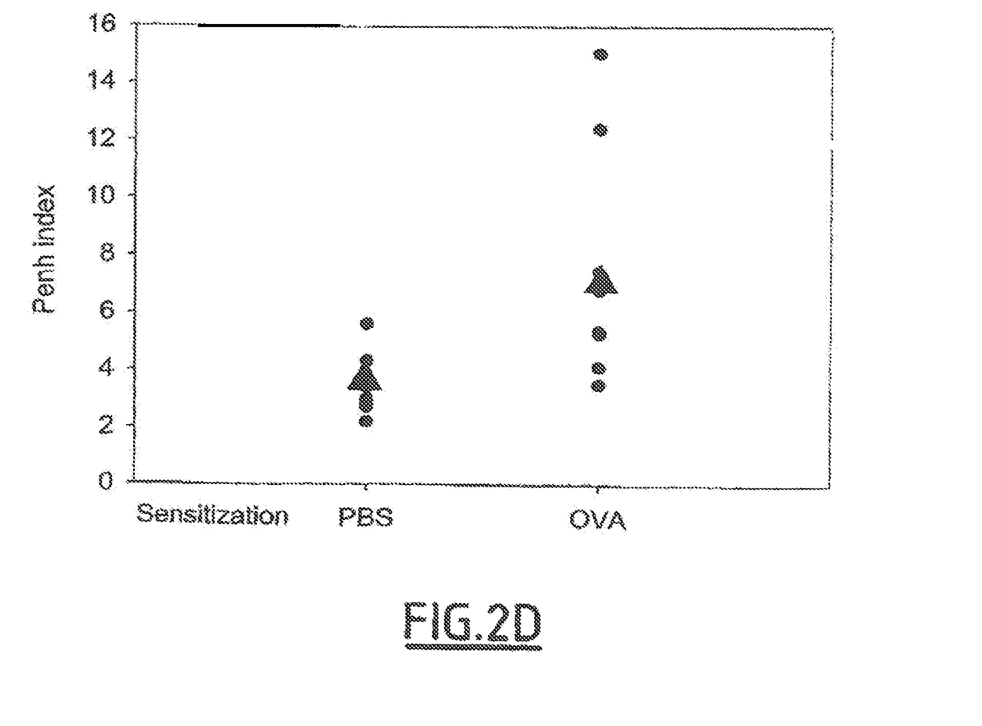
Figure 2E:
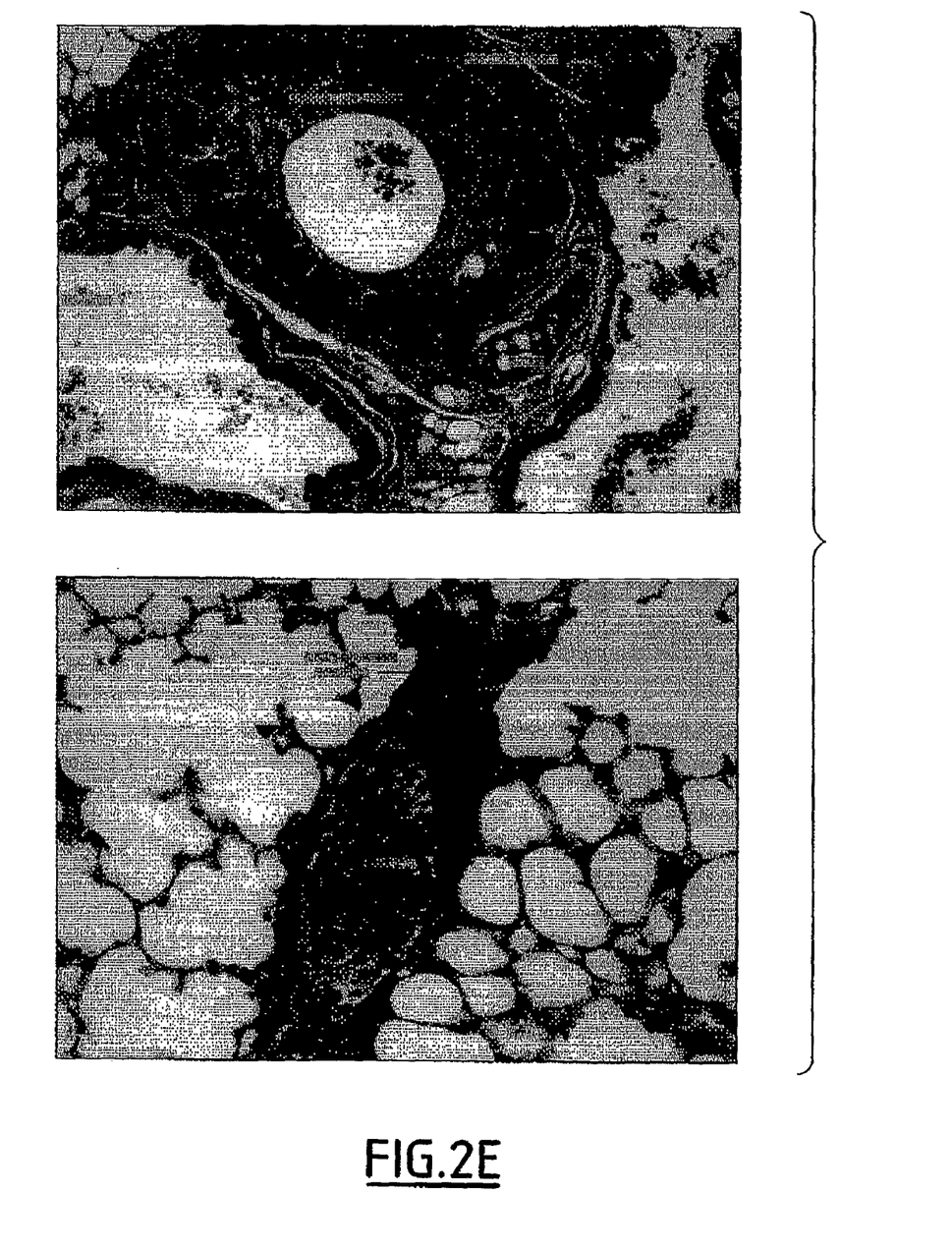

Mice, immunized i.p. with OVA absorbed to Al(OH)$_3$ and subsequently exposed to an OVA solution via aerosol, were analysed for their humoral, cellular, and respiratory responses and inflammation. The sensitization procedure has been shown to induce OVA-specific IgG1 and IgE, but little IgG2a antibodies in serum (FIGS. 2A and 2B). In accordance with the production of allergen-specific IgE antibodies, spleen cells from the OVA-sensitization mice displayed strong Th2 profile in response to OVA (FIG. 2C). OVA-sensitized mice present airway hyperresponsiveness to methacholine when compared to PBS-treated mice (FIG. 2D). Finally, the sensitization protocol has been shown to induce specific cellular infiltration of the lung and bronchial mucus secretion (FIG. 2E).

2. Sublingual Tolerization in a Therapeutic Model of Type I Allergy

After having sensitized the mice, the inventors have tested different protocols of tolerization and particularly the capacity of candidate adjuvants to upregulate antigen-specific regulatory T cell responses and to accelerate the tolerance induction by the sublingual route. *Lactobacillus plantarum* and 1α,25-dihydroxyvitamin D3 in combination with dexamethasone have been tested as adjuvants for upregulation of antigen-specific regulatory T cell responses.

Figure 3A:
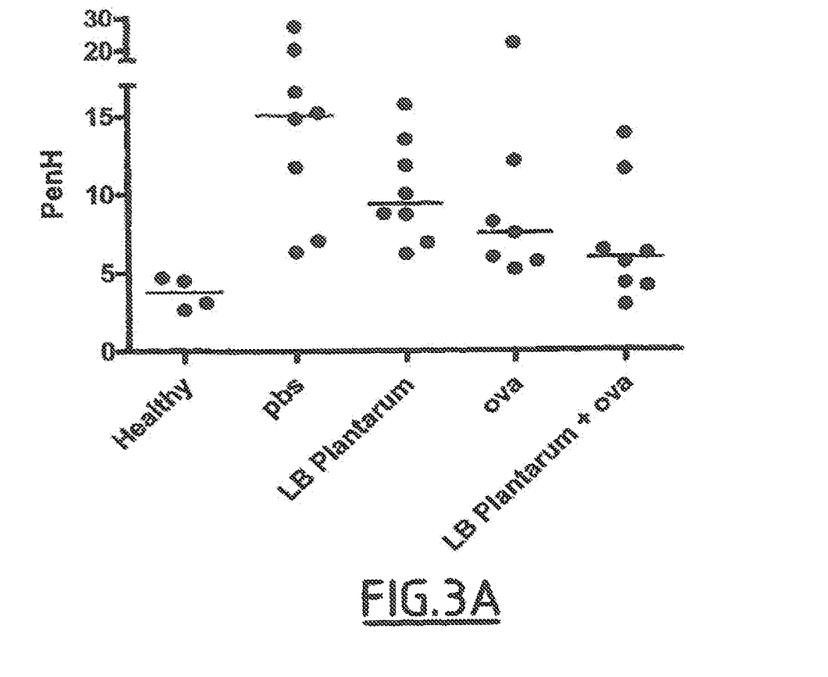
Figure 3B:
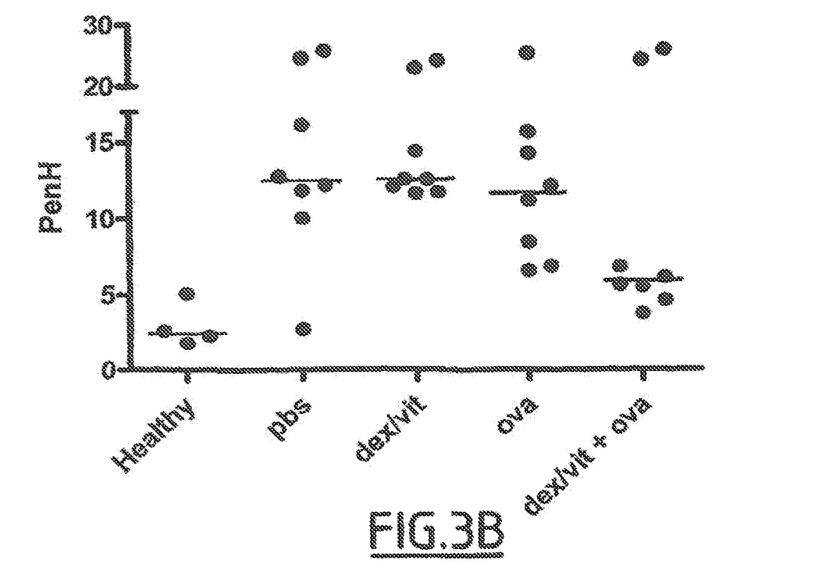

Sublingual treatment with OVA administered together with *L. plantarum* (FIG. 3A) or 1α,25-dihydroxyvitamin D3 plus dexamethasone (FIG. 3B) (group 3) led to a reduction of airway responsiveness as compared to PBS-treated mice (group 1) or animals treated with OVA alone (group 2).

Figure 4A:
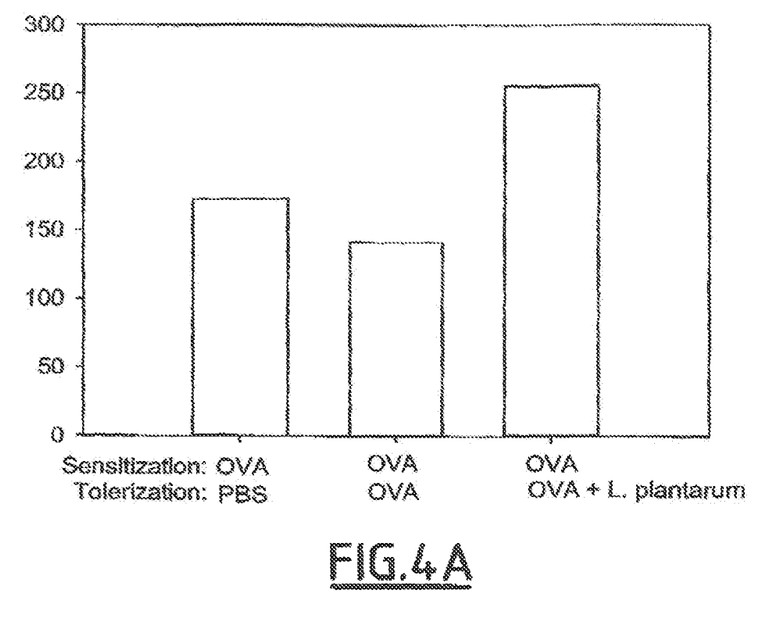
Figure 4B:
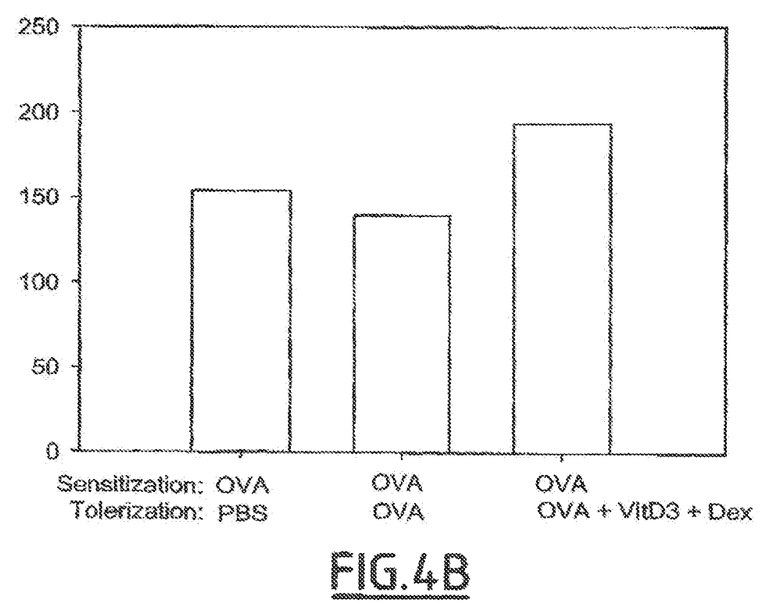

Finally, TGF-β production was enhanced in supernatant of spleen cell cultures of mice treated with OVA and *L. plantarum* (FIG. 4A) or 1α,25-dihydroxyvitamin D3 plus dexamethasone (FIG. 4B) compared to PBS-treated mice or animals treated with OVA alone.

3. Sublingual Tolerization in a Prophylactic Model of Type I Allergy

Sublingual desensitization is also tested in a murine prophylactic model of asthma Briefly, Balb/c mice are sublingually administered with an adjuvant to be tested (1α,25-dihydroxyvitamin D3+dexamethasone) in association with an antigen (OVA) (500 μg) 2 times per week during 4 weeks prior to being sensitized and challenged by OVA.

Results indicate that pre-treatment of mice with OVA+ adjuvant according to the invention is liable to induce a reduction of airway responsiveness following subsequent sensitization.

4. Murine Models of Sensitization with Birch Pollen and House Dust Mite

The adjuvants according to the invention are tested in murine model of sensitization either to birch pollen or house dust mite and also seem promising for preventing or treating allergies with these allergens.

The invention claimed is:

1. A method for inducing an antigen-specific tolerance in an individual in need thereof, comprising the sublingual or perlingual co-administration to the individual of therapeutically effective amounts of a first composition comprising an adjuvant that is a combination of dexamethasone with vitamin D3 or 1α,25-dihydroxyvitamin D3; and a second composition comprising at least an antigen against which antigen-specific tolerance is to be induced, and wherein the adjuvant and the antigen are co-administered in separate compositions either simultaneously or consecutively.

2. The method of claim 1, wherein the compositions elicit or improve antigen-specific regulatory T cell responses.

3. The method of claim 1, wherein the compositions induces production of IL10 by T cells.

4. A method for treating an allergy in an individual in need thereof, comprising co-administering by sublingual or perlingual route to the individual therapeutically effective amounts of a first composition comprising an adjuvant that is a combination of dexamethasone with vitamin D3 or 1α,25-dihydroxyvitamin D3; and a second composition comprising at least an allergen to which the individual has developed a sensitivity; and wherein the adjuvant and the allergen are co-administered in separate compositions either simultaneously or consecutively.

5. A method for treating an autoimmune disease in an individual in need thereof, comprising co-administering by sublingual or perlingual route to the individual therapeutically effective amounts of a first composition comprising an adjuvant that is a combination of dexamethasone with vitamin D3 or 1α,25-dihydroxyvitamin D3; and a second composition comprising at least an antigen to which the patient has developed or is likely to develop a sensitivity; and wherein the adjuvant and the antigen are co-administered in separate compositions either simultaneously or consecutively.

6. A method for preventing graft rejection in an individual in need thereof, comprising co-administering by sublingual or perlingual route to the individual therapeutically effective amounts of a first composition comprising an adjuvant that is a combination of dexamethasone with vitamin D3 or 1α,25-dihydroxyvitamin D3; and a second composition comprising at least an allergen to which the patient has developed or is likely to develop a sensitivity; and wherein the adjuvant and the antigen are co-administered in separate compositions either simultaneously or consecutively.

7. The method of claim 1, wherein said antigen is an allergen.

8. The method of claim 1, wherein said antigen is a protein allergen selected from the group consisting of a protein allergen of the genus *Dermatophagoides*; a protein allergen of the genus *Felis*; a protein allergen of the genus *Ambrosia*; a protein allergen of the genus *Lolium*; a protein allergen of the genus *Cryptomeria*; a protein allergen of the genus *Alternaria*; a protein allergen of the genus *Alder*; a protein allergen of the genus *Betula*; a protein allergen of the genus *Blomia*; a protein allergen of the genus *Quercus*; a protein allergen of the genus *Olea*; a protein allergen of the genus *Artemisia*; a protein allergen of the genus *Plantago*; a protein allergen of the genus *Parietaria*; a protein allergen of the genus *Canine*; a protein allergen of the genus *Blattella*; a protein allergen of the genus *Apis*; a protein allergen of the genus *Cupressus*; a protein allergen of the genus *Juniperus*; a protein allergen of the genus *Thuya*; a protein allergen of the genus *Chamaecyparis*; a protein allergen of the genus *Periplaneta*; a protein allergen of the genus *Agropyron*; a protein allergen of the genus *Secale*; a protein allergen of the genus *Triticum*; a protein allergen of the genus *Cynorhodon*; a protein allergen of the genus *Dactylis*; a protein allergen of the genus *Festuca*; a protein allergen of the genus *Poa*; a protein allergen of the genus *Avena*; a protein allergen of the genus *Holcus*; a protein allergen of the genus *Anthoxanthum*; a protein allergen of the genus *Arrhenatherum*; a protein allergen of the genus *Agrostis*; a protein allergen of the genus *Phleum*; a protein allergen of the genus *Phalaris*; a protein allergen of the genus *Paspalum*; and a protein allergen of the genus *Sorghum*.

9. The method of claim 1, wherein said antigen is a protein allergen selected from the group consisting of Bet v I; Bet v II; Blo t I; Blo t III; Blo t V; Blo t XII; Cyn d I; Der p I; Der p II; Der p III; Der p VII; Der f I; Der f II; Der f III; Der f VII; Fel d I; Amb a I.1; Amb a I.2; Amb a I.3; Amb a I.4; Amb a II; Lol p I; Lot p II; Lol p III; Lol p IV; Lol p IX; Cry j I; Cry j II; Can f I; Can f II; Jun s I; Jun v I; Jun a I; Jun a II; Dac g I; Dac g V; *Poa* p I; Phl p I; Phl p V; Phl p VI and Sor h I.

10. The method of claim 1, wherein said antigen is a protein involved in an auto-immune disease or graft rejection.

11. The method of claim 1, which comprises sublingual administration of the immunogenic composition to the individual.

12. The method of claim 1, which comprises perlingual administration of the compositions to the individual.

13. The method of claim 4, wherein said antigen is a protein allergen selected from the group consisting of a protein allergen of the genus *Dermatophagoides*; a protein allergen of the genus *Felis*; a protein allergen of the genus *Ambrosia*; a protein allergen of the genus *Lolium*; a protein allergen of the genus *Cryptomeria*; a protein allergen of the genus *Alternaria*; a protein allergen of the genus *Alder*; a protein allergen of the genus *Betula*; a protein allergen of the genus *Blomia*; a protein allergen of the genus *Quercus*; a protein allergen of the genus *Olea*; a protein allergen of the genus *Artemisia*; a protein allergen of the genus *Plantago*; a protein allergen of the genus *Parietaria*; a protein allergen of the genus *Canine*; a protein allergen of the genus *Blattella*; a protein allergen of the genus *Apis*; a protein allergen of the genus *Cupressus*; a protein allergen of the genus *Juniperus*; a protein allergen of the genus *Thuya*; a protein allergen of the genus *Chamaecyparis*; a protein allergen of the genus *Periplaneta*; a protein allergen of the genus *Agropyron*; a protein allergen of the genus *Secale*; a protein allergen of the genus *Triticum*; a protein allergen of the genus *Cynorhodon*; a protein allergen of the genus *Dactylis*; a protein allergen of the genus *Festuca*; a protein allergen of the genus *Poa*; a protein allergen of the genus *Avena*; a protein allergen of the genus *Holcus*; a protein allergen of the genus *Anthoxanthum*; a protein allergen of the genus *Arrhenatherum*; a protein allergen of the genus *Agrostis*; a protein allergen of the genus *Phleum*; a protein allergen of the genus *Phalaris*; a protein allergen of the genus *Paspalum*; and a protein allergen of the genus *Sorghum*.

14. The method of claim 4, wherein said antigen is a protein allergen selected from the group consisting of Bet v I; Bet v II; Blo t I; Blo t III; Blo t V; Blo t XII; Cyn d I; Der p I; Der p II; Der p III; Der p VII; Der f I; Der f II; Der f III; Der f VII; Fel d I; Amb a I.1; Amb a I.2; Amb a I.3; Amb a I.4; Amb a II; Lol p I; Lot p II; Lol p III; Lot p IV; Lol p IX; Cry j I; Cry j II; Can f I; Can f II; Jun s I; Jun v I; Jun a I; Jun a II; Dac g I; Dac g V; *Poa* p I; Phl p I; Phl p V; Phl p VI and Sor h I.

15. The method of claim 4, which comprises sublingual administration of the immunogenic composition to the individual.

16. The method of claim 4, which comprises perlingual administration of the immunogenic composition to the individual.

* * * * *